US012569371B2

(12) United States Patent
Drury et al.

(10) Patent No.: US 12,569,371 B2
(45) Date of Patent: Mar. 10, 2026

(54) STERILIZATION OF MEDICAL DRESSINGS WITH ENHANCED ANTIMICROBIAL PROPERTIES

(71) Applicant: HYDROFERA, LLC, Manchester, CT (US)

(72) Inventors: Thomas J. Drury, Narragansett, RI (US); John E. O'Gara, Ashland, MA (US); Christopher Hanson, East Hampton, CT (US); John Mantese, Ellington, CT (US)

(73) Assignee: HYDROFERA, LLC, Manchester, CT (US)

( * ) Notice: Subject to any disclaimer, the term of this patent is extended or adjusted under 35 U.S.C. 154(b) by 312 days.

(21) Appl. No.: 18/198,469

(22) Filed: May 17, 2023

(65) Prior Publication Data

US 2023/0285197 A1 Sep. 14, 2023

Related U.S. Application Data

(62) Division of application No. 16/602,440, filed on Oct. 7, 2019, now abandoned.

(60) Provisional application No. 62/749,902, filed on Oct. 24, 2018.

(51) Int. Cl.
| | |
|---|---|
| *A61F 13/01* | (2024.01) |
| *A61F 13/00* | (2006.01) |
| *A61F 13/05* | (2024.01) |
| *A61L 2/081* | (2026.01) |
| *A61L 2/20* | (2006.01) |
| *A61L 2/206* | (2026.01) |
| *A61L 15/22* | (2006.01) |
| *A61L 15/24* | (2006.01) |
| *A61L 15/26* | (2006.01) |
| *A61L 15/42* | (2006.01) |
| *A61L 15/44* | (2006.01) |
| *A61L 15/58* | (2006.01) |
| *A61F 13/42* | (2006.01) |
| *A61F 13/53* | (2006.01) |
| *A61L 103/05* | (2026.01) |
| *A61L 103/15* | (2026.01) |

(52) U.S. Cl.
CPC ................. *A61F 13/00063* (2013.01); *A61F 13/00059* (2013.01); *A61F 13/01017* (2024.01); *A61F 13/01021* (2024.01); *A61F 13/05* (2024.01); *A61L 2/081* (2013.01); *A61L 2/20* (2013.01); *A61L 2/206* (2013.01); *A61L 15/225* (2013.01); *A61L 15/24* (2013.01); *A61L 15/26* (2013.01); *A61L 15/425* (2013.01); *A61L 15/44* (2013.01); *A61L 15/58* (2013.01); *A61F 2013/00336* (2013.01); *A61F 2013/429* (2013.01); *A61F 2013/530649*

(2013.01); *A61L 2103/05* (2026.01); *A61L 2103/15* (2026.01); *A61L 2300/404* (2013.01)

(58) Field of Classification Search
None
See application file for complete search history.

(56) References Cited

U.S. PATENT DOCUMENTS

| | | | |
|---|---|---|---|
| 3,572,340 A | 3/1971 | Lloyd et al. | |
| 4,525,166 A | 6/1985 | Leclerc | |
| 5,811,471 A | 9/1998 | Shanbrom | |
| 5,908,693 A | 6/1999 | Delgado et al. | |
| 6,207,875 B1 | 3/2001 | Lindqvist et al. | |
| 7,569,742 B2 | 8/2009 | Haggstrom et al. | |
| 9,084,845 B2 | 7/2015 | Adie et al. | |
| 9,480,830 B1 | 11/2016 | Azocar | |
| 9,974,890 B2 | 5/2018 | Hudspeth et al. | |
| 10,046,096 B2 | 8/2018 | Askem et al. | |
| 11,147,696 B2 | 10/2021 | Scanlon et al. | |
| 11,273,077 B2 | 3/2022 | Kubek | |
| 2006/0030632 A1* | 2/2006 | Krueger | ................ A61L 15/225 521/50 |
| 2010/0160881 A1 | 6/2010 | Lin et al. | |
| 2010/0324510 A1 | 12/2010 | Andresen et al. | |
| 2011/0045072 A1* | 2/2011 | da Cruz | .................. A61L 15/46 424/617 |

(Continued)

FOREIGN PATENT DOCUMENTS

| | | |
|---|---|---|
| WO | 2010056544 A1 | 5/2010 |
| WO | 2017075320 A1 | 5/2017 |

OTHER PUBLICATIONS

U.S. Appl. No. 16/602,439; Final Office Action dated Sep. 21, 2023; 30 pages.
U.S. Appl. No. 16/602,519; Final Office Action dated Jun. 29, 2023; 21 pages.
U.S. Appl. No. 18/196,079; Final Office Action dated Sep. 12, 2024; 15 pages.
U.S. Appl. No. 18/196,079; Non-Final Office Action dated May 8, 2024; 21 pages.

(Continued)

*Primary Examiner* — Brian Gulledge
(74) *Attorney, Agent, or Firm* — CANTOR COLBURN LLP

(57) ABSTRACT

The present invention relates to a sponge dressing for treating wounds comprised of a polymer sponge containing a plurality of antimicrobial dyes with at least one dye being gram positive and at least one other dye being gram negative and a silicon adhesive secured to a sponge surface. The sponge dressing can be exposed initially to gamma radiation and later sterilized by ethylene oxide or alternatively it can be sterilized by ethylene oxide and later irradiated by gamma radiation. The sponge dressing has a morphology characterized by an average pore throat diameter of 0.5-500 μm and a porosity ranging from about 60% to about 99.5%. The sponge dressing can also contain at least one biofilm reducing agent, at least one chelating agent and an ionic and non-ionic surfactant.

14 Claims, 3 Drawing Sheets

(56)  References Cited

U.S. PATENT DOCUMENTS

| 2011/0060204 | A1 | 3/2011 | Weston |
| 2011/0091353 | A1 | 4/2011 | Burgess et al. |
| 2011/0092958 | A1 | 4/2011 | Jacobs |
| 2011/0178451 | A1 | 7/2011 | Robinson et al. |
| 2011/0230849 | A1 | 9/2011 | Coulthard et al. |
| 2012/0078155 | A1 | 3/2012 | Bowman et al. |
| 2012/0157750 | A1 | 6/2012 | Robinson et al. |
| 2013/0032967 | A1 | 2/2013 | Wang et al. |
| 2014/0018654 | A1 | 1/2014 | Drury |
| 2014/0163490 | A1 | 6/2014 | Locke et al. |
| 2014/0275864 | A1* | 9/2014 | Drury ................. A61F 13/0203 |
| | | | 600/309 |
| 2015/0351970 | A1 | 12/2015 | Dagger et al. |
| 2016/0361478 | A1 | 12/2016 | Eddy |
| 2017/0296383 | A1 | 10/2017 | Friedman et al. |
| 2018/0093013 | A1 | 4/2018 | Dehnad et al. |
| 2018/0257059 | A1 | 9/2018 | Heo et al. |
| 2018/0263823 | A1 | 9/2018 | Chatterjee |
| 2018/0264181 | A1 | 9/2018 | Gregory et al. |
| 2018/0289872 | A1 | 10/2018 | Coulthard et al. |
| 2018/0296395 | A1 | 10/2018 | Kubek |
| 2018/0296397 | A1 | 10/2018 | Askem et al. |
| 2018/0296712 | A1 | 10/2018 | Dobrinsky et al. |
| 2018/0338945 | A1 | 11/2018 | Sambasivam |
| 2018/0344533 | A1 | 12/2018 | Rovaniemi |
| 2018/0369462 | A1 | 12/2018 | Anderson et al. |
| 2020/0078499 | A1 | 3/2020 | Gadde et al. |
| 2020/0129339 | A1 | 4/2020 | Drury et al. |
| 2020/0129340 | A1 | 4/2020 | Drury et al. |
| 2020/0129648 | A1* | 4/2020 | Drury ..................... A61L 15/26 |
| 2020/0345888 | A1 | 11/2020 | O'Gara et al. |
| 2021/0100929 | A1 | 4/2021 | Dizio et al. |
| 2023/0310219 | A1 | 10/2023 | Drury et al. |

OTHER PUBLICATIONS

Chrzanowska et al. "Elaboration of small-diameter vascular prostheses-Selection of appropriate sterilisation method." Journal of Applied Polymer Science 131.18 (2014). 10 pages.

Hsiao et al. "The influence of γ irradiation and ethylene oxide treatment on the release characteristics of biodegradable poly(lactide-co-glycolide) composites." Polymer degradation and stability 97.5 (2012): 715-720.

* cited by examiner

STERILIZATION OF MEDICAL DRESSINGS WITH ENHANCED ANTIMICROBIAL PROPERTIES

RELATED APPLICATIONS

This application is a divisional application of application Ser. No. 16/602,440, filed Oct. 7, 2019, which claims priority and benefits from provisional patent application No. 62/741,839 filed Oct. 5, 2018, the contents of which in their entirety are herein incorporated by reference.

STATEMENT REGARDING FEDERALLY SPONSORED RESEARCH OR DEVELOPMENT

None

REFERENCE TO SEQUENCE LISTING, A TABLE OR A COMPUTER PROGRAM LISTING COMPACT DISC APPENDIX

None.

BACKGROUND OF THE INVENTION

1. Field of Invention

The present dressing relates to a method of sterilization of medical devices and more particularly, medical dressings. More particularly, the present invention relates to sterilization with gamma radiation and ethylene oxide of foamed polymers containing antimicrobial positive and negative dyes and coated with a silicone adhesive.

2. Background of the Invention

The term sterilization refers to the elimination of micro-organisms such as fungi, bacteria and viruses, or a reduction in the bioburden of an item where bioburden refers to the number of micro-organisms with which the item is contaminated. The degree of sterilization is typically measured by a sterility assurance level (SAL) which refers to the probability of a viable microorganism being present on a product unit after sterilization.

There are a number of sterilization procedures. The broad categories of sterilization include heat, chemicals, and irradiation. An example of using heat to sterilize is autoclaving of medical instruments. Cooking or canning food is also another application of using heat for sterilization. A number of chemicals can be used for sterilization including ozone, chlorine dioxide, ethylene oxide, and hydrogen peroxide. Irradiation includes exposure to gamma rays, x-rays, or an electron beam.

Many medical devices undergo terminal sterilization; that is sterilization occurs in the final packaged product. Thus, the sterilization operation may have a negative impact on the material of the device, and/or any active biocidal agents contained in the device. The present invention is directed to methods of sterilization that limit or eliminate some of these negative impacts of sterilization on the effectiveness of device, and particularly methods involving ethylene oxide sterilization.

Ethylene oxide (EO, EtO) sterilization is a broadly used terminal sterilization method for medical devices.

EO sterilization and irradiation as a terminal sterilization can also cause limitations for medical devices or more specifically wound dressings containing antimicrobial positive and negative dyes. One example is a limitation on materials that can be used as different materials have their properties changed by sterilization. In the case of wound dressings, medical silicone adhesives and silicon rubbers are excluded from use in gamma terminally sterile products, e.g. as cover dressings, despite their excellent clinical performance. Therefore, a wound dressing comprised of an antimicrobial positive and negative dyed wound dressing and a silicone adhesive is not known in the prior art.

In U.S. Patent Application Publication Number US2013/ 0032967 published Feb. 7, 2013 describes a method of EO sterilization on polymeric stents where the temperature is kept below 40° C. to limit or eliminate negative impacts on polymeric stents caused by ethylene oxide sterilization.

Hsiao et al. (Polymer Degradation and Stability, 2012, 97, 715) reported EO sterilization to have a substantial effect on the release pattern of drugs embedded in a biodegradable polymer scaffold. In one case, the total drug-releasing period for the BO-treated samples was much shorter than that of untreated controls, and the overall amount of released antibiotic was less.

Chrzanowski et al. (Journal of Applied Polymer Science, 2014, 131, 40812) reported that EtO sterilization resulted in destruction of poly (1-lactide-co-glycolide) (PLGA) vascular prostheses, where radiation sterilization did not affect the material.

Polymeric based wound dressings made from e.g. polyvinyl alcohol (PVA) or polyurethane polyether (PU) polymers and that contain antimicrobial positive and negative dyes are terminally sterilized using irradiation, e.g. Hydrofera® Blue (Hydrofera, LLC), RTD® Wound Dressing (Keneric Healthcare), NovaGran™ Blue Plus Dressing™ (Principle Business Enterprises, Inc.). In all known cases, the use of medical silicone adhesives is excluded from the device's design.

None of the aforementioned references attempt to increase the effect of antimicrobial positive and negative dyes or allow the uses of silicone adhesives with sterile product to prevent or preclude biofilm from forming on wounds.

Wounds often have multiple barriers to healing. Wound healing and infection is influenced by the relationship between the ability of bacteria to create a stable, prosperous community within a wound environment and the ability of the host to control the bacterial community. Since bacteria are rapidly able to form their own protective microenvironment (biofilm) following their attachment to a surface, the ability of the host to control these organisms is likely to decrease as the biofilm community matures. Within a stable biofilm community, interactions between aerobic and anaerobic bacteria are likely to increase their net pathogenic effect, enhancing their potential to cause infection and delay healing. Over the last few years, some have linked biofilm to chronic wounds. Microscopic evaluation or chronic wounds showed well organized biofilm with extracellular polymeric substance adhered around colony bacteria in at least 60% of the chronic wounds.

There is thus a need for new methods of making dressings and other medical devices with absorbed or impregnated therapeutic agents, more specifically antimicrobial positive and negative dyes, where the medical devices' performance is not impaired by an EO sterilization step. The above noted teachings do not aid in the resolution of a number of practical difficulties that are resolved by the present invention.

SUMMARY OF THE INVENTION

The present invention describes Ethylene Oxide terminally sterilizing sterile dressings with enhanced antimicrobial properties. Enhanced antimicrobial properties are achieved through the method of using gamma irradiation as a processing step on the dyed medical device prior to final assembly and terminal EO sterilization.

The invention allows for incorporation of non-gamma stable parts, e.g. silicones, in the final assembled product followed by terminal EO sterilization of the finished device. The gamma irradiation process step prior to the terminal EO sterilization surprisingly gives improved antimicrobial properties in comparison to the same device without the prior irradiative step. In a preferred embodiment, the device is an antibacterial dressing. The invention is directed to methods and processes for making these terminal EO sterile antimicrobial positive and negative dyed medical devices.

It is an object of the invention to make sterilized dressings and medical devices with integrated antimicrobial positive and negative dyes using silicone adhesives.

It is another object of the invention to make a sterilized antimicrobial positive and negative dye containing sponge dressing whereby the dye effectiveness against micro-organisms is enhanced by the sterilization process.

It is yet another object of the invention to provide an effective wound dressing comprising antimicrobial polymer for the treatment of chronic wounds that is capable of donating and absorbing moisture and exudate for optimal wound healing.

BRIEF DESCRIPTION OF THE DRAWINGS

The present invention will be described with reference to the appended Figures, in which.

Figure 1:
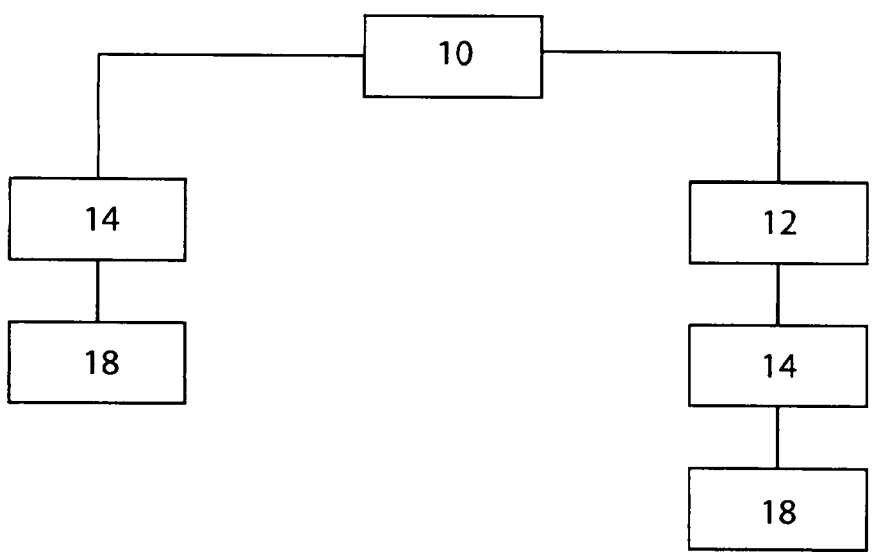
FIG. 1 is a schematic block drawing of gamma radiation with subsequent EO sterilization.

These and other objects, advantages, and novel features of the present invention will become apparent when considered with the teachings contained in the detailed disclosure along with the accompanying drawings.

DESCRIPTION OF THE INVENTION

Use of the singular herein includes the plural and vice versa unless expressly stated to be otherwise, or obvious from the context that such is not intended. That is, "a" and "the" refer to one or more of whatever the word modifies. For example, "a device" includes one device, two devices, etc. Likewise, "a polymer" may refer to one, two or more polymers, and "the polymer" may mean one polymer or a plurality of polymers. By the same token, words such as, without limitation, "devices" and "polymers" would refer to one device or polymer as well as to a plurality of devices or polymers unless, again, it is expressly stated or obvious from the context that such is not intended.

In the same manner, any ranges presented are inclusive of the end-points. For example, "a temperature between 10° C. and 30° C." or "a temperature from 10° C. to 30° C." includes 10° C. and 30° C., as well as any temperature in between.

Also, words of approximation when used herein such as, without limitation, "about" "substantially," "essentially" and "approximately" mean that the word or phrase modified by the term need not be exactly that which is written but may vary from that written description to some extent. The extent to which the description may vary will depend on how great a change can be instituted and have one of ordinary skill in the art recognize the modified version as still having the properties, characteristics and capabilities of the modified word or phrase. In general, but with the preceding discussion in mind, a numerical value herein that is modified by a word of approximation may vary from the stated value by plus or minus 15%, unless expressly stated otherwise.

The aspects of the present invention are described in the following paragraphs along with their preferred embodiments. In the below text the term "wound" is to be understood in its broadest sense, i.e. as any exterior part of a human or animal body that may be in need of treatment, particularly antibacterial treatment. Examples of wounds in the present context includes but are not limited to: Any laceration to the skin, such as a wound, a chronic wound, a burn wound, a cut, wounds associated with dermatological conditions, grafts, pressure wounds, traumatic wounds, underlying infections with fistulation from bone, joint or soft tissue. The present invention uses polymeric foam or sponges treated with antibacterial or antimicrobial material which is placed over the wound.

Wound Dressing Materials

The wound dressing may be a foam or sponge material and may be polymeric in composition where the polymer can be a synthetic substance, a natural substance or combinations thereof. In one example the synthetic polymer can be polyvinyl formal (PVF), polyvinyl acetal, polyurethane, polyester, polyethylene terephthalate or a mixture of polymers. The natural polymer material can be either animal or plant derived, for example, collagen, or chitosan. The preferred sponge material is polyvinyl acetal, polyurethane or polyvinyl formal.

The foam or sponge has a morphology characterized by an average pore throat diameter of 0.5-500 μm, a fluid retention of 5.5-25.0 mL fluids/g porous material, a density of 0.05-0.15 g polymer/cm$^3$ porous material, and a porosity of 60-99.5%. The cell structure is characterized as open I interconnected with through pores that can be evaluated by techniques such as capillary flow porometry and liquid extrusion porosimetry.

Figure 4:
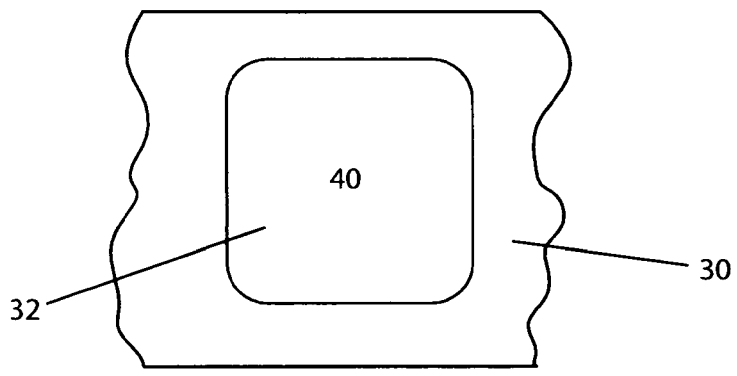
FIG. 4 is a plan view of the inventive dressing showing the silicone sheet extending beyond the sponge material.

The silicon adhesive is attached to a silicone film sheet 30 and is applied to a planar surface 32 of the sponge material dressing 40. The film sheet may extend beyond the dressing where it can adhere to the skin surface and keep the dressing in place as is shown in FIG. 4.

While the preferred embodiment of the invention is directed toward treated sponge dressings, it is envisioned as being used on other medical devices such as polyurethane catheters which are highly prone to infection.

Dyes & Antimicrobial Agents

The dyes are clinically safe and have antimicrobial properties. The term "antimicrobial" is defined as having the ability to destroy or inhibit the growth of microorganisms, and comprises one or more of the following: antibacterial, antifungal, antiprotozoal, and antiviral. The inventive sterile dressing for treating wounds is made from a polymer sponge containing a plurality of antimicrobial dyes with at least one dye being gram positive and at least one other dye being gram negative. The dressing is exposed to both gamma radiation and ethylene oxide, which increase the sterilibility and allow a silicon adhesive to be secured to said sponge surface.

Dyes can include, for example, triaryl or diarylmethanes, methylene blue, toluidine blue, methylene violet, azure A, azure B, azure C, brilliant cresol blue, thionin, methylene green, bromcresol green, crystal violet, acridine orange, brilliant green, acridine yellow, quinacrine, trypan blue, trypan red and mixtures of these dyes. In a preferred embodiment, the dyes are methylene blue and crystal violet. The above dye listing contains gram positive- and gram negative dyes. Dyes of both charges are utilized to combat a large family of bacteria having gram positive and gram negative characteristics. Other antimicrobials agents can include e.g. chlorhexidine, rifampicin, sparfloxacin and triclosan.

Radiation Activation after Terminal Sterilization

In another embodiment, the activation by irradiation occurs after terminal sterilization with EO.

In the case of devices with parts that are not compatible with the radiation type, masking techniques may be used to shield the non-compatible parts of the sterile device from radiation exposure.

In another irradiation method for devices with parts that are not compatible with the radiation type, radiation sources with spatial coherence (e.g. lasers) that allows for selectively activating areas of the device that are stable to radiation exposure. These radiation sources may also have high temporal coherence.

There is currently a need for effective medical products that include active substances which inhibit the growth of and/or kill bacteria, in particular there is a need for wound care products and methods that inhibit the growth of and/or kill biofilm forming bacteria more efficiently.

Example 1

Antibacterial Activity Test

Antibacterial activity is measured in the following manner.

1. Prepare duplicate samples of the dyed and processed sponge dressings material in 5×5 cm swatches.
2. Prepare duplicate samples in 5×5 cm swatches of the undyed sponge dressings as controls.
3. Inoculate each sample (treated and control) with 5.0 mL of approximately 1.0E+06 CFU/mL of each specified challenge organism.
4. Challenge organisms are: *Staphylococcus aureus* (SA, ATCC #6538), *Escherichia coli* (EC, ATCC #11775), and *Pseudomonas aeruginosa* (PA, ATCC #9027). These bacteria are three of the five most common bacteria found in wound infections with *Staphylococcus aureus* (SA, ATCC #6538) being the most common.
5. Incubate samples in a humidified atmosphere for 24 hours at 37° C.
6. After this initial incubation period express the fluid from each sample, and plate aliquots of serial dilutions to Tryptic-Soy Agar and re-incubate for at least an additional 24 hours at 37° C.
7. Following incubation, all plates are removed and the total colony forming units enumerated.
8. Assess each treated material versus the original inoculum level.

Example 2

PU foam, PVA foam and PVF foam were dyed with methylene blue (MB) and crystal violet (CV), washed with water and dried. The dyed foams or sponge dressings 10 were then processed through gamma irradiation 12 and EO 14 steps to obtain test units 18 in the order shown in FIG. 1.

Gamma Irradiation 25-36 kilogray (kGy) dose achieved by controlled exposure to Cobalt 60 and EO Terminal Sterilization Pre-Conditioning: NIA Cycle Temperature: 108±5° F.

Cycle Humidity: approximately 30% RH

Sterilant (EO) Concentration: approximately 600 mg/L

These EO process conditions represent the absolute minimum achievable set points that can reproducibly achieve a sterility assurance level (SAL) of $10^{-6}$ at a production scale.

After the terminal sterilization step, as shown in FIG. 1, the dyed foam material samples were measured for antibacterial properties using the method described in Example 1, with the data being shown in Table 1. The data in Table 1 shows that gamma irradiation as a process step undertaken prior to EO sterilization gave better antibacterial activity than the EO sterilized only test samples.

TABLE 1

| Polymer | MB Load (mg/g) | CV Load (mg/g) | Process Gamma | Terminal EO | Average Log Reduction (CFU/mL) vs Inoculum | | |
|---|---|---|---|---|---|---|---|
| | | | | | SA | EC | PA |
| PVA | 0.50 | 0.80 | | X | 3.76 | 2.77 | 1.65 |
| PVA | 0.50 | 0.80 | X | X | 6.18 | 6.27 | 6.18 |
| PU | 0.08 | 0.60 | | X | 6.06 | 1.40 | 1.98 |
| PU | 0.08 | 0.60 | X | X | 6.18 | 6.27 | 6.18 |
| PU¹ | 0.49 | 0 | | X | −0.39 | −1.38 | −1.40 |
| PU¹ | 0.49 | 0 | X | X | 2.44 | −0.24 | 6.16 |
| PU | 0.27 | 0.35 | | X | 2.63 | −0.47 | 1.69 |
| PU | 0.27 | 0.35 | X | X | 3.73 | 6.20 | 6.16 |
| PU | 0.11 | 0.60 | | X | 2.04 | −0.61 | 6.14 |
| PU | 0.11 | 0.60 | X | X | 6.21 | 6.20 | 6.16 |
| PU | 0.00 | 0.55 | | X | 1.72 | −0.64 | 6.14 |
| PU | 0.00 | 0.55 | X | X | 6.21 | 6.20 | 6.16 |

The Table 1 notation PU¹ in the Polymer column denotes an example using only one dye.

This data shows surprising results with an increase in antibacterial dye effectiveness for both the PVA and PU sponges which is normally reduced during the EO sterilization step. This allows the use of silicone adhesive on the sponges treated with EO sterilization. As previously noted this Table includes data on polyurethane which includes single dye samples.

Example 3

Figure 2:
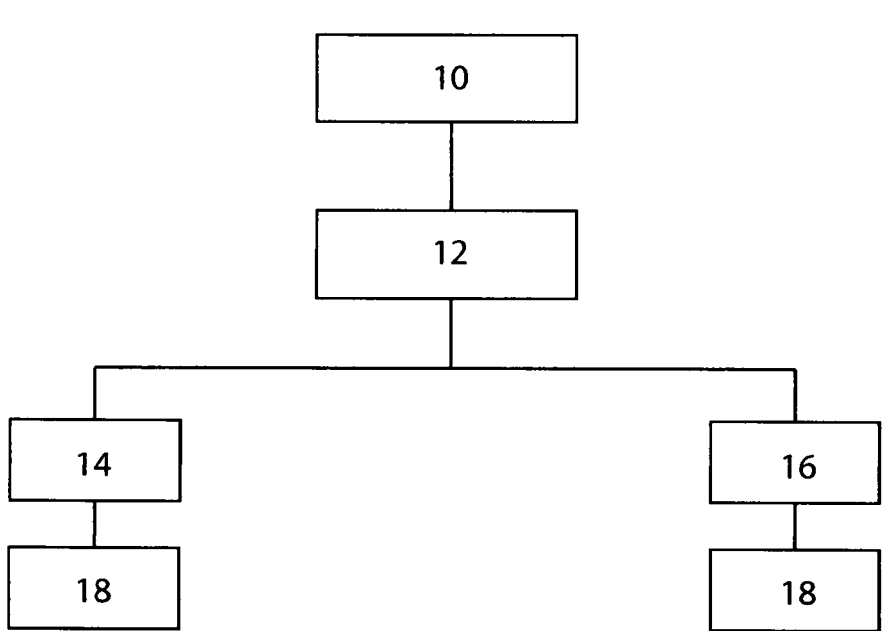
FIG. 2 is a schematic block drawing of gamma radiation with two comparative EO sterilization methods.

PU foam was dyed with methylene blue (MB) and crystal violet (CV), washed with water and dried. The dyed foam 10 was then processed using gamma irradiation 12 per Example 2 followed by EO 14 as described in Example 2 or by standard EO sterilization 16 conditions to obtain test samples 18 as listed below. The processing order is outlined in FIG. 2.

Standard Cycle EO Terminal Sterilization

Dwell Time Limits: 24-48 hours, 50-80% RH, 40-52° C.

Cycle Temperature Range: 108±5° F.

Cycle Humidity: <55% RH

Sterilant (EO) Concentration: approximately 600 mg/L

After the terminal step, the dyed foams were measured for antibacterial properties using the method described in Example 1. Antibacterial performance for the samples is found in Table 2.

TABLE 2

| | MB Load | CV Load | EO Method | EO Method | Average Log Reduction (CFU/mL) vs Inoculum | | |
|---|---|---|---|---|---|---|---|
| Polymer | (mg/g) | (mg/g) | Example 2 | Example 3 | SA | EC | PA |
| PU | 0.29 | 0.35 | X | | 6.27 | 6.24 | 6.25 |
| PU | 0.29 | 0.35 | | X | 6.23 | −0.78 | 6.21 |
| PU | 0.08 | 0.60 | X | | 6.27 | 6.24 | 6.25 |
| PU | 0.08 | 0.60 | | X | 6.23 | 0.20 | 6.21 |

Example 4

Figure 3:
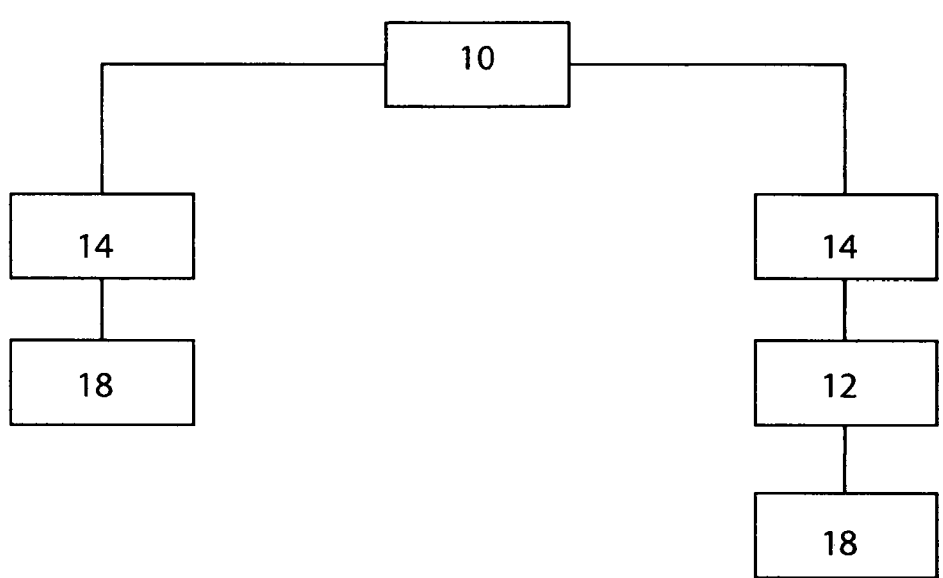
FIG. 3 is a schematic block drawing like FIG. 2 with EO sterilization before the gamma sterilization step.

PU foam was dyed with methylene blue (MB) and/or crystal violet (CV), washed with water and dried. The dyed foams 10 were then processed as noted in example 2 conditions with the EO 14 and/or gamma irradiative 12 steps in the order shown in FIG. 3.

After the final step, the dyed foams were measured for antibacterial properties using the method described in Example 1, and the data is found in Table 3. The data shows that gamma irradiation 12 as a process step after EO sterilization gave better antibacterial activity than the EO sterilized only samples.

TABLE 3

| Poly-mer | MB Load | CV Load | Terminal | Process | Average Log Reduction (CFU/mL) vs Inoculum | | |
|---|---|---|---|---|---|---|---|
| | (mg/g) | (mg/g) | EO | Gamma | SA | EC | PA |
| PU | 0.08 | 0.60 | X | | 6.06 | 1.40 | 1.98 |
| PU | 0.08 | 0.60 | X | X | 3.00 | 6.20 | 6.13 |
| PU | 0.49 | 0 | X | | −0.39 | −1.38 | −1.40 |
| PU | 0.49 | 0 | X | X | 6.26 | 4.08 | 6.13 |
| PU | 0.27 | 0.35 | C | | 2.63 | −0.47 | 1.69 |
| PU | 0.27 | 0.35 | X | X | 6.26 | 6.26 | 6.13 |
| PU | 0.11 | 0.60 | X | | 2.04 | −0.61 | 6.14 |
| PU | 0.11 | 0.60 | X | X | 6.26 | 6.26 | 6.13 |
| PU | 0.00 | 0.55 | X | | 1.72 | −0.64 | 6.14 |
| PU | 0.00 | 0.55 | X | X | 6.26 | 6.26 | 3.92 |

Example 5

Radiation Activation Prior to Dye Addition. White PU foam was processed using gamma radiation at a dose of 25-36 kGy. The foam was then dyed as described in Example 2 or 3 and sterilized by EO as described in Example 2 and 3 and the data found in the tables.

TABLE 4

| | MB Load | CV Load | EO | Process | Average Log Reduction (CFU/mL) vs Inoculum | | |
|---|---|---|---|---|---|---|---|
| Polymer | (mg/g) | (mg/g) | Method | Gamma | SA | EC | PA |
| PU | 0.29 | 0.35 | Ex2 X | X | 6.27 | 6.24 | 6.25 |
| PU | 0.29 | 0.35 | Ex3 X | X | 6.23 | −0.78 | 6.21 |

Example 6

Thermal Characterization of Radiation Activated Polymers. Radiation activated polymers are characterized by a proportionally larger population of mobile polymer segments vs. their EO only sterilized analogs. Said population of more mobile segments may be distinguished from those without using differential scanning colorimetry, where differences in glass transition temperature (Tg) profiles are measured. In one example, the radiation activated polymers have one or more glass transition endotherms, and the EO only analogs have none detected. In another example, the radiation activated polymers show an increase of greater than ° C. in the Tg temperature in going from the 1st to 2nd heat cycle vs the EO only analog which shows no change. Without wishing to be bound by theory, a change in the population of mobile polymer segments may translate to a more therapeutically effective antibacterial agent release from the material.

Dyed foam samples were processed through gamma irradiative and/or EO steps as described in Example 2. When both irradiation and EO steps were conducted, irradiation preceded EO.

Differential Scanning calorimetry (DSC) was performed using a TA Q2000 Differential Scanning calorimeter in combination with TA Universal Analysis software. At least 2 mg of each sample was 'placed in hermetically sealed pans for analysis. The samples were each analyzed in duplicate and the average value is reported in Table 5. Polyurethane samples were cooled to −80° C., then heated to 200° C. at 20° C./min, cooled back to −80° C. at 20° C./min. and heated again to 200° C. at 20° C./min. Polyvinyl alcohol samples were heated from 30° C. to 90° C. at 20° C./min, cooled back to 30° C. at 20° C./min and heated again to 90° C. at 20° C./min. Where more than one endotherm was observed, only the major endotherm is reported.

TABLE 5

| Dyed Polymer | Sample ID | Step 1 Gamma | Step 2 EO | Step 3 Gamma | (° C.) | | |
|---|---|---|---|---|---|---|---|
| | | | | | 1st Heat | 2nd Heat | 1st to 2nd |
| PVA | 042519.4 | X | | | 67.01[1] | 1.40 | 3.37 |
| PVA | 042519.5 | X | X | | 66.88 | 6.20 | 2.22 |
| PVA | 042519.6 | | X | | ND | ND | ND |
| PVA | 062619.1 | | X | X | 62.45[2] | 56.97 | 5.48 |
| PU | 042519.7 | X | | | −30.30 | −0.47 | 8.27 |
| PU | 042519.8 | X | X | | −31.07 | −28.18 | 2.89 |
| PU | 042519.9 | | X | | −31.81 | −31.81 | 0 |
| PU | 062619.2 | | X | X | −29.30 | −19.99 | 9.31 |

[1]A second minor endotherm observed on the first heat only at 48.56° C.

[2]A second minor endotherm observed on the first heat only at 52.44° C.

Biofilm Reduction Agents

Biofilm reduction agents are clinically safe and help remove biofilm by breaking up the film structure. Such agents are incorporated onto the sponge prior to the sterilization steps.

As an example, enzymes are used to target and break down the extracellular polymer substances of the biofilm and include amylase enzymes (e.g. amyloglucosidase, bacterial amylo novo), protease enzymes (e.g. savinase and everlase) fibrinolytic agents (e.g. plasmin, streptokinase, and nattokinase, and TrypLE), deoxyribonuclease I, glycoside hydrolase dispersin B, and cellulase.

Also chelating agents are used in the sponge body to sequester the metals that crosslink polysaccharides in the biofilm including ethylenediaminetetraacetic acid (EDTA), citrates, phosphonates and phosphonic acids.

Surfactants are used to solubilize the biofilm macromolecules, including ionic and non-ionic surfactants. Ionic surfactants may be negatively charged, positively charged, or zwitterionic, and include alkyl sulfates (e.g. sodium dodecyl sulfate), alkyl carboxylates, (e.g. sodium stearate), tertiary or quaternary alkyl ammoniums (e.g. cetrimonium bromide, cetrimonium chloride, cetrimonium stearate), 3-[(3-cholamidopropyl)dimethylammonio]-1-propane-sulfonate (CHAPS). Non-ionic surfactants may include polyethylene glycol, polyethylene oxide, Triton, Tergitol, Pluronics, IGEPELS, Tweens, fatty acid esters.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What is claimed is:

1. A process of sterilizing a dressing, the process comprising:

exposing the dressing to gamma radiation; and sterilizing the dressing with ethylene oxide, wherein:

the process comprises exposing the dressing to gamma radiation prior to sterilizing the dressing with ethylene oxide, the dressing comprises a polymer sponge comprising polyvinyl formal polyvinyl acetal, polyurethane, or a mixture of said polymers and containing a gram negative dye and a gram positive dye, and the gamma irradiation increases antibacterial dye effectiveness of the polymer sponge treated with ethylene oxide sterilization.

2. The process of claim 1, wherein exposing the dressing to gamma radiation comprises exposing the dressing to gamma radiation for a period suitable to apply gamma radiation ranging from about 5 to about 36 kilogray to the dressing.

3. The process of claim 1, wherein the gram positive dye and the gram negative dye comprise a triaryl or diarylmethane, methylene blue, toluidine blue, methylene violet, azure A, azure B, azure C, brilliant cresol blue, thionin, methylene green, bromcresol green, crystal violet, acridine orange, brilliant green, acridine yellow, quinacrine, trypan blue, trypan red, or a combination thereof.

4. The process of claim 3, wherein:

the gram negative dye comprises methylene blue; and the gram positive dye comprises crystal violet.

5. The process of claim 1, wherein the dressing further comprises a silicon adhesive.

6. The process of claim 1, wherein the polymer sponge comprises polyvinyl formal.

7. The process of claim 1, wherein the polymer sponge comprises polyvinyl acetal.

8. The process of claim 1, wherein the polymer sponge comprises polyurethane.

9. The process of claim 1, wherein the polymer sponge has an average pore throat diameter of 0.5-500 μm.

10. The process of claim 1, wherein the polymer sponge has a fluid retention of 5.5-25.0 mL fluids/g porous material.

11. The process of claim 1, wherein the polymer sponge has a density of 0.05-0.15 g polymer/cm$^3$ porous material.

12. The process of claim 3, wherein exposing the dressing to gamma radiation improves antimicrobial effectiveness of the gram positive dye and the gram negative dye in the dressing against *Staphylococcus aureus* above antimicrobial effectiveness of the gram positive dye and the gram negative dye in the dressing against *Staphylococcus aureus* treated with only ethylene oxide.

13. The process of claim 3, wherein exposing the dressing to gamma radiation improves antimicrobial effectiveness of the gram positive dye and the gram negative dye in the dressing against *Escherichia coli* above antimicrobial effectiveness of the gram positive dye and the gram negative dye in the dressing against *Escherichia coli* treated with only ethylene oxide.

14. The process of claim 3, wherein exposing the dressing to gamma radiation improves antimicrobial effectiveness of the gram positive dye and the gram negative dye in the dressing against *Pseudomonas aeruginosa* above antimicrobial effectiveness of the gram positive dye and the gram negative dye in the dressing against *Pseudomonas aeruginosa* treated with only ethylene oxide.

* * * * *